United States Patent [19]

Hallgren et al.

[11] 4,046,914
[45] Sept. 6, 1977

[54] THERAPEUTICALLY ACTIVE SUBSTITUTED SATURATED AND MONO-AND POLYUNSATURATED ALKYL-GLYCERYLETHERS

[75] Inventors: Bo Erik Hallgren, Molndal; Gunnel Anna Maria Stallberg, Goteborg, both of Sweden

[73] Assignee: Astra Nutrition AB, Molndal, Sweden

[21] Appl. No.: 553,683

[22] Filed: Feb. 27, 1975

Related U.S. Application Data

[60] Continuation of Ser. No. 152,976, June 14, 1971, abandoned, which is a division of Ser. No. 689,789, Dec. 12, 1967, abandoned.

[51] Int. Cl.$^2$ .................. A61K 31/23; A61K 31/22
[52] U.S. Cl. ...................................... 424/312; 424/311
[58] Field of Search ................................ 424/312, 311

[56] References Cited

PUBLICATIONS

Hallgren et al.-Acta Chemica Scand., vol. 21, (1967), pp. 1519-1529.

*Primary Examiner*—Sam Rosen
*Attorney, Agent, or Firm*—Brumbaugh, Graves, Donohue & Raymond

[57] ABSTRACT

Pharmaceutical preparations containing alkyl and alkenyl glycerol ethers substituted in the side chain and esters thereof having the general formula

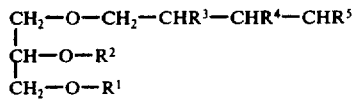

wherein $R^1$ and $R^2$ are the same or different in each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups of at most seven carbon atoms, and $R^5$ is selected from the group consisting of straight, branched, alkyl and alkenyl groups of 4–21 carbon atoms. The compounds are useful as antibiotics in the treatment of infectious diseases and for inhibiting the growth of tumors.

30 Claims, No Drawings

THERAPEUTICALLY ACTIVE SUBSTITUTED SATURATED AND MONO-AND POLYUNSATURATED ALKYL-GLYCERYLETHERS

This application is a continuation of our copending application Ser. No. 152,976 filed June 14, 1971, which in turn was a divisional application of Ser. No. 689,789 filed Dec. 12, 1967, now both abandoned.

The present invention relates to alkyl- and alkenyl-glyceryl ethers substituted in the side chain and esters thereof and pharmaceutical preparations and compositions thereof as well as methods for the synthetical preparation and isolation from natural products of such compounds.

It is known that unsubstituted alkyl- and alkenyl-glyceryl ethers and their esters which have been isolated from liver oils of Greenland shark and dog-fish in certain concentrations and dosages have stimulating effect on the formation of blood cells in the bonemarrow. They have been employed as haematopoetic agents in cancer therapy (vide Astrid Brohult: Alkoxyglyceroles and their use in radiation treatment, Acta Radiol (1963) Suppl. 223). After the shark liver oils have been prepurified by removal of hydrocarbon fractions and saponifiable material there is obtained a residual fraction mainly consisting of α-glyceryl ethers with saturated and monounsaturated fatty alcohols containing 14–22, possibly 24, carbon atoms, for the main part chimylalchol of 16 C-atoms, batylalcohol of 18 carbon atoms and selachylalcohol unsaturated in 9–10 position and having 18 carbon atoms in the alkyl chain. These glyceryl ethers are also growth promoting agents as they stimulate the growth of certain bacteria such as Lactobacillus lactis.

It has now been shown that the α-glyceryl ether fraction obtained from shark liver oils besides said normal unsubstituted ethers also contains a small amount, about 3% by weight, of more polar ethers consisting of a mixture of alkyl- and alkenylglyceryl ethers substituted in 2-position in the alkyl resp. alkenyl chain by a methoxy group. Thus the small methoxy-substituted glyceryl ether fraction was found to contain about 60% by weight of (2-methoxy-4-hexadecenyl)-α-glycerylether, 15% by weight of (2-methoxy-hexadecyl)-α-glyceryl ether and 20% by weight of (2-methoxy-4-octadencyl)-α-glyceryl ether. The following ethers were identified in the mixture.

| Number of carbon atoms in the radical | Number of olefinic bonds |
|---|---|
| 14 | 0 |
| 15 | 0 |
| 16 | 0 |
| 16 | 1 |
| 17 | 0 |
| 17 | 1 |
| 18 | 0 |
| 18 | 1 |
| 18 | 2 |
| 18 | 3 |
| 19 | 0 |
| 19 | 1 |
| 20 | 0 |
| 20 | 1 |
| 20 | 2 |
| 20 | 3 |
| 22 | 1 |
| 22 | 2 |
| 22 | 3 |
| 22 | 5 |
| 22 | 6 |

It has now surprisingly been found that these earlier unknown methoxy-substituted glyceryl ethers show propertis differing from those of previously isolated and identified glyceryl ethers. Thus they exhibit an antibiotic activity against several types of bacteria, especially Coryne-bacterium hofmanni, Diplococcus pneumoniae, Staphylococcus Oxford, pyogenes A and pyogenes H, Streptococcus pyogenes and Streptococcus viridans. The activity has been compared with that of nitrofurantoin (Furadantin) and bensylpenicillin and found to be about the same as for nitrofurantoin. The earlier known glyceryl ethers did not exhibit any antibiotic effect. Most remarkable is the cytostatic effect which has been shown in vitro against cultures of cancer cells, namely the type He La cells, on one hand and in vivo in mice on the other.

At in vitro tests using the methoxyalkylglyceryl ethers in a concentration of 100 μg/ml the cells were killed all together within 72 hours. At a concentration of 25 μg/ml the methoxyalkylglyceryl ethers isolated from liver oil of Greenland shark as well as a synthetically prepared 2-methoxyhexadecyl-α-glyceryl ether acted clearly cytostatically and the natural product had completely suppressed the growth within about 8 days, while the synthetic product had done this only after about 15 days.

While the total glyceryl ether fraction including the small amount of methoxy-substituted ethers isolated from shark liver oil stimulated the growth of transplantated mammary cancer in mice at a diet containing one product of glyceryl ethers a diet of 0.5% of methoxy-substituted glyceryl ethers exhibited a growth retarding effect upon the tumors during a period of 15 days. The formation of metastases in the lungs were also suppressed. No difference was observed in consumption of food or bodyweight between the test animals and a group of control animals. The methoxy-substituted glyceryl ethers proved to have no influence upon the number of red and white blood cells in concentrations of 0.25% of the food. This is of particular interest because as above said they have cytostatic and cancer retarding effects, which consequently are exerted with no influence upon the normal increase in or formation of red and white blood cells, not even at such comparatively high doses as 0.25% of the food quantity.

Accordingly the present invention provides a therapeutically, particularly antibiotically and cytostatically active or cancer retarding agent or preparation, which as active ingredient contains at least one glyceryl ether of the formula

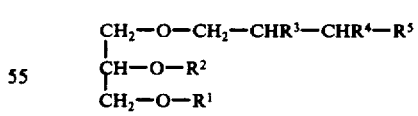

wherein $R^1$ and $R^2$ are the same or different and each selected from the group consisting of hydrogen and alifatic acyl groups of at most 24, preferably 14–18 carbon atoms; one of $R^3$ and $R^4$ is hydrogen and the other being a straight or branched saturated or unsaturated alkoxy group of at most 7 carbon atoms and $R^5$ is selected from straight and branched saturated and mono- and polyunsaturated alkyl groups of 4 to 21 carbon atoms. The pharmaceutical preparations or compositions according to the invention should contain at least 5% by weight, preferably at least 10% by weight, of at least one of said glyceryl ethers in association with a pharmaceutically acceptable carrier, which can be a fatty oil or possibly an aqueous solution. The carrier may possibly be or contain one or more unsubstituted alkyl- and/or akenyl glyceryl ethers. The preparation may thus be composed of a natural product concentrated to at least 5% by weight of methoxy-substituted glyceryl ethers.

The present invention further provides a process for the concentration of compounds of the formula

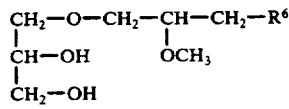

II wherein $R^6$ is selected from straight and branched alkyl saturated and unsaturated groups of 9-21 carbon atoms, from naturally occuring lipid products containing α-glyceryl ethers, such as liver oils from Greenland shark, dog-fish, rat-fish (shimacra monstrosa) or products therefrom enriched in glyceryl ethers, which process comprises a distribution of a lipid product, preferably after prepurification by removal of hydro-carbons and saponifiable constituents, between two media forming different phases comprising an operation consisting of A. a preferably repeated extraction using two at least to some extent non-miscible liquids of different densities in which liquids the product is soluble, said liquids being kept in contact with each other, one of said liquids being selected from the group consisting of essentially non-polar solvents such as petroleum ether, carbon tetrachloride, cyclic aliphatic hydrocarbons, aromatic hydrocarbons and mixtures thereof and the other liquid being selected from the group consisting of optionally aquous polar organic solvents such as alcohols, ketones, nitriles and mixtures thereof; or B. chromatography of the lipid product in a solvent on a solid adsorbent selected from the group consisting of silicic acid and deactivated aluminum oxide and eluting the adsorbent using in a first step a low polar solvent such as a mixture of a minor amount of ether in petroleum ether and using in a second step a more polar solvent such as ether; or C. treating the lipid product dissolved in a suitable solvent such as methanol with a substance such as urea, capable of forming inclusion compounds with some part of the glyceryl ether mixture; or D. fractionated crystallization from a polar solvent selected from the group consisting of water, water miscible lower alifatic alcohols water miscible ketones and mixtures containing two or more of said solvents;

whereafter, if desired, a further enrichment of the methoxy-ethers may be procured by vacuum distillation or preparative gas chromatography.

The distribution may be carried out for instance in a column or a centrifuge or by repeated shaking of the phases with each other in continuous or step wise counter-flow, for instance by the way of Craig's technic. Suitable pairs of liquids in these cases may be heptane and methanol or acetone containing 10-30% preferably 20% by water and hexane and aqueous (10-30%) acetonitrile, carbon tetrachloride and aqueous (10-30%) methanol.

A separation by adsorption chromatography may be performed by contacting a solution of the product in a solvent with an adsorbent in solid form for instance silicic acid or deactivated aluminum oxide and eluting the adsorbent with suitable solvents whereafter the eluate is divided into one enriched part and one depleted part at which the process is carried out continuously or in batches until the desired concentration of the enriched solution is obtained.

The concentration may also be carried out by treating the glyceryl ether mixture dissolved in a suitable solvent such as methanol with a compound, for instance urea, which can form inclusion compounds which some part of the glyceryl ether mixture at which the unsubstituted glyceryl ethers, particularly the saturated ones, may be precipitated by urea as clatrates which are separated off whereafter the enriched product is obtained from the solution. A concentration of upto 10% has thus been achieved which is about the same as obtained by means of fractionated crystallization.

Antibiotically and cytostatically active or cancer retarding compounds of the formula

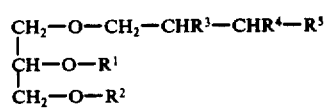

III wherein $R^1$ and $R^2$ are the same or different and each selected from the group consisting of hydrogen and alifatic acyl groups of at most 24, preferably 14–18 carbon atoms; one of $R^3$ and $R^4$ is hydrogen and the other being a straight or branched, saturated or non-saturated alkoxy group of at most 7 carbon atoms and $R^5$ is selected from straight and branched saturated and mono- and polyunsaturated alkyl groups of 4 to 21 carbon atoms, which method comprises reacting a compound of the formula

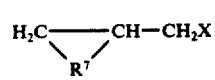

IV with a compound of the formula $$Y - CH_2 - CHR^{31} - CHR^{41} - R^{51} \qquad V$$

in which formulas $R^{31}$ is delected from $R^3$ and an atom or a group of atoms capable of being transformed into $R^3$ by methods known per se, $R^{41}$ is selected from $R^4$ and an atom or a group of atoms capable of being transformed into $R^4$ by methods known per se, one of $R^{31}$ and $R^{41}$ being hydrogen, $R^{51}$ is selected from $R^5$ and an atom or a group of atoms capable of being transformed into $R^5$ by methods known per se, $R^7$ is selected from the class consisting of —O—, a carbon-carbon bond and

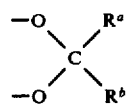

wherein $R^a$ is a member of the class consisting of H and alkyl, $R^b$ is a member of the class consisting of alkyl and aryl and wherein $R^a$ and $R^b$ together may form a ring which may contain a heteroatom; X and Y is a pair selected from the group of pairs of atom groups consisting of a. Hal, and —OM, b. arylsulphonyl and —OM,
c. alkylsulphonyl and —OM, and
d. hydroxy and hydroxy, and in which pairs of atom groups M is a positively charged atom or groups of atoms preferably K, Na or Li, Hal means halogen, preferably Cl and Br, to the formation of a compound of the formula

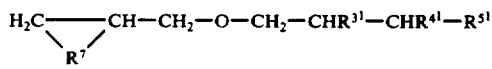

whereafter if any of $R^{31}$, $R^{41}$ and $R^{51}$ differs from $R^3$, $R^4$ and $R^5$ respectively, the different group is transformed into the predetermined group, whereafter the group

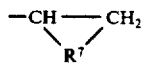

is transformer to the group

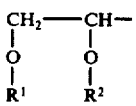

by means of methods known per se.

According to one embodiment X is selected from —OM and hydroxy, Y is p-toluenesulphonyl and $R^7$ is

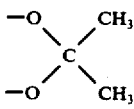

wherein M has the meaning given above.

According to one preferred embodiment X is selected from —OK and hydroxy and $R^7$ is

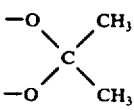

and the splitting of the isopropylidene compound is carried out by acid hydrolysis.

According to still another embodiment of the present invention X and Y are hydroxyl groups and water is split off by means of a water-removing agent, suitably a dehydration catalyst such as sulphuric acid possibly at a low concentration.

Suitably the compound of the formula IV is coupled to a compound of formula V wherein $R^{31}$, $R^{41}$ and $R^{51}$ are $R^3$, $R^4$, $R^5$ respectively, but according to another embodiment an alkyl or alkenyl glyceryl ether having a chain of insufficient length may be prepared whereafter said chain is prolonged by methods known per se to the desired length. In this case $R^{51}$ represents an aliphatic hydrocarbon radical having the terminal carbon atom of the radical substituted with a reactive atom or group of atoms suitable for an alkylation of the terminal carbon atom or having a terminal double or triple bond whereafter the etherified α-glyceryl ether thus formed is reacted with an alkylating agent capable of transforming $R^{51}$ to $R^5$. The end carbon atom may be substituted with halogen, e.g. bromine or chlorine or possibly iodine. The prolongation may be performed for instance by means of an alkyl halogenide and coupling be performed in a manner known per se by using alkali metal or by using an organometallic compound. When $R^{51}$ is an alifatic hydrocarbon radical having a double or triple bond at the terminal carbon atom the lengthening of the hydrocarbon chain is carried out by means of organometallic compounds.

According to still another embodiment one of $R^{31}$ and $R^{41}$ is an atom or a group of atoms capable of being transformed into $R^3$ respectively $R^4$ by methods known per se and the other being hydrogen. $R^{31}$ respectively $R^{41}$ may be a halogen atom, preferably chlorine, and the compound formed is reacted with an alcoholate $MR^3$ respectively $MR^4$, wherein M, $R^3$ and $R^4$ have the meaning given above. This is exemplified by the following formulas

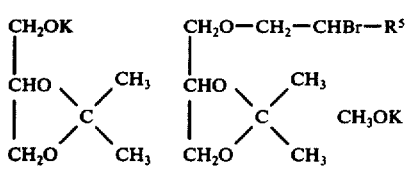

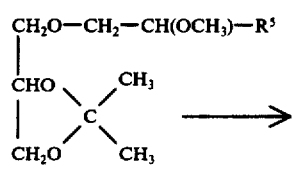

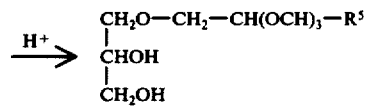

It is suitable to start from glycerol and since etherification of only one of the hydroxy groups in end position of the glycerol is to be carried out the hydroxy groups in β- and γ-position must be protected. This can of course be performed in different ways and a convenient method is to protect the glycerol by internal ether formation

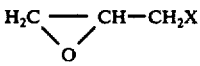

For instance glycidol or epichlorhydrine which are epoxides of glycerol, with a free α-hydroxylgroup or with this group replaced by chlorine, respectively may be used as starting material.

Another way of protecting the glycerol is to react it with a carbonyl compound for instance a ketone or an aldehyde, preferably acetone, or any ketone which preferably reacts with vicinal hydroxy groups and the protecting group is split off in a manner known per se when the ether formation between X and Y is completed.

Saturated glyceryl ethers may also be obtained from an allyl compound for instance allyl chloride or allyl bromide which is etherified to the formation of an allyl alkyl ether, $CH_2 = CH — CH_2OR$ which may be oxidized to glyceryl ether and further treated or directly transformed into the desired glyceryl ether derivative in a manner known to a man skilled in the art.

The syntheses described above have been performed using an alifatic alcohol etherified in 2- or 3-position or a functional derivative thereof and if there is no such derivative available it may be prepared for instance by treatment of a carboxylic acid or carboxylic ester halogenated preferably with bromine or chlorine, possibly iodine in 2- respectively 3-position with an alcoholate of the alcohol of the hydrocarbon group which shall be introduced for the ether formation in 2- respectively 3-position of the alkyl or alkenyl group. Then the acid respectively the ester is reduced to the corresponding alcohol.

The ether in the side chain may of course be prepared by etherification of a hydroxy group in 2- or 3-position.

As an illustration of methods for the preparation of glyceryl ethers etherified in 3-position of the side chain the following formulas may be given:

$$CH_3-(CH_2)_n-CHO + BrOH_2-COOCH_3$$

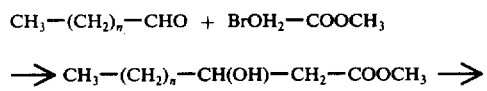
$$\rightarrow CH_3-(CH_2)_n-CH(OH)-CH_2-COOCH_3 \rightarrow$$

etherification using
a. alkyl halogenide or alkylsulphate etc. or
b. $BF_3 + CH_2N_2$, or
c. substituation of OH by halogen and reacting with e.g. an alcoholate

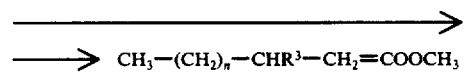
$$\longrightarrow CH_3-(CH_2)_n-CHR^3-CH_2=COOCH_3$$

and further treatment as above.

The second step may be obtained by reduction of a 3-keto ester to a 3-hydroxy ester or by conversion of an α,β-unsaturated ester to a 2,3-epoxy ester which is converted into a 3-hydroxy ester.

Especially when preparing an alkenyl glyceryl ether the following embodiment may be used which however also may be employed for the preparation of saturated compounds. The unsaturated or saturated alifatic alcohol etherified in 2- or 3-position with a particular hydrocarbon group or a functional derivative of the alcohol is prepared by reacting 1,2-dihalogenethylalcohol respectively 1,3-dihalogenpropyl alcohol etherified in 1- position with the particular hydrocarbon group with an α-halogen hydrocarbon compound with the desired number of carbon atoms at which the halogen preferably is Br, Cl or possibly I. As an example of this synthesis the following reaction may be mentioned

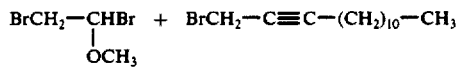
$$BrCH_2-CHBr + BrCH_2-C\equiv C-(CH_2)_{10}-CH_3$$
$$\phantom{BrCH_2-}|$$
$$\phantom{BrCH_2-}OCH_3$$

wherein the triple bond may be replaced by a double bond or a single bond. The bromine atom attached to the same atom as the methoxy group is activated by the presence of the oxygen. The dibromo ether is conveniently prepared by addition of bromine to vinyl methyl ether. The α-brominated hydrocarbon compound may be obtained according to any of the following ways:

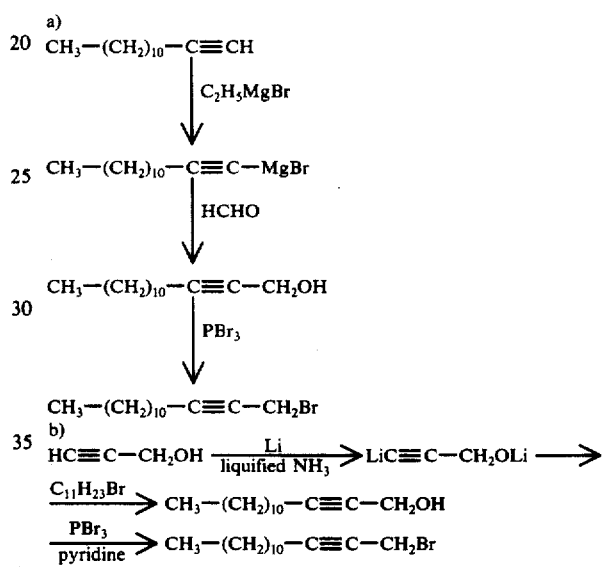

If more saturated end products are desired, more saturated compounds may be used as starting material or the triple bond may be more or less strongly reduced.

In a step-wise construction of the side chain the embodiment illustrated by the following formulas may be used:

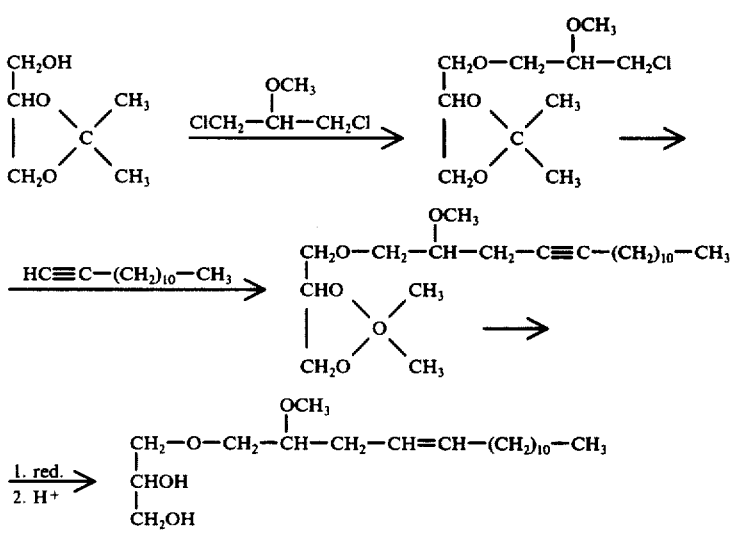

The invention is further illustrated by the following examples.

EXAMPLE 1

4 g of unsaponifiable material from shark liver oil (obtained from the mother liquid after precipitation with urea) containing about 10 % of methoxy-substituted glyceryl ethers were distributed into tubes 2–7 in a counter-current distribution apparatus according to Craig. The apparatus consisted of 200 tubes each holding 50 ml (25 ml of stationary bottom phase and 25 ml of movable upper phase). As the bottom phase 80 % methanol and as the upper phase n-hexane was employed (the upper and the bottom phases were brought into equilibrium with each other beforehand by shaking in a separating funnel). The concentrations of the methoxy-substituted glyceryl ethers were observed by means of thin layer chromatography. After 170 shakings the solutions in the tubes only containing material other than methoxy glyceryl ethers were replaced with new bottom and upper phases whereafter another 170 shakings were performed. The solutions in the tubes containing materials of 37 no value" were replaced once more with clean bottom and upper phases. After additional 200 shakings 297 mg of material was obtained containing about 90 % of methoxy-substituted glyceryl ethers and 10 % of ordinary glyceryl ethers.

EXAMPLE 2

Liver oil from Greenland shark was freed from some volatile components by molecular distillation. About 10 % of the oil was distilled off. The residue was subjected to alkaline hydrolysis in 1 N ethanolic KOH by boiling under reflux for 1 h. The unsaponifiable material containing the glycerol ethers was extracted from the saponification mixture by diethyl ether.

Silicic acid specially prepared for the chromatography of lipids was obtained from Calbiochem and was used without further pretreatment. The nonsaponifiable material was dissolved in a mixture of 5 % diethyl ether in light petroleum (b.p. 60°–80° C) and applied to columns in amounts of about 15 mg per g of silicic acid. A fraction mainly consisting of hydrocarbons and cholesterol was eluted by 5 % diethyl ether in light petroleum. The glyceryl ethers were then eluted by diethyl ether. The effluents were collected in 20 ml fractions at which the ordinary glyceryl ethers first appeared immediately followed by the methoxy-substituted glyceryl ethers.

The following methoxy-substituted glyceryl ethers were identified in the effluents by mass spectrometry: 1-O-(2-methoxy-4-hexadecenyl)-glycerol, 1-O-(2-methoxyhexadecyl)-glycerol, 1-O-(2-methoxy-4-octadecenyl)-glycerol.

EXAMPLE 3

2-Methoxyhexadecyl p-toluenesulfonate (2.5 g) was condensed with 1,2-isopropylidene glycerol (1.1 g) by the method described by Gupta, S.C. and Kummerov, F.A: J. Org. Chem. 24, (1959), 409. The crude product was purified by silicic acid chromatography using light petroleum (b.p. 40°–60° C) as solvent. About 45 % of the product consisted of 2,3-O- isopropylidene compound of the glyceryl ether.

The isopropylidene compound (78 mg) was treated with 0.5 N HCl (50 $\mu$l) at 100° C for 3 hours during continuous shaking. The glyceryl ether was extracted by dimethyl ether and after evaporation of the dimethyl ether a colourless liquid (72 mg) was obtained. Thin-layer chromatography showed that the splitting of the isopropylidene compound was nearly complete. The product was purified by silicic acid chromatography, the less polar contaminants were removed by elution with 5 % diethyl ether in light petroleum and the free glyceryl ether was then eluted with ether, 83 % of the crude product consisted of free glyceryl ether.

Methoxy hexadecyl p-toluenesulphonate used as starting material was prepared in the following way:

2-Bromohexadecanoic acid (m.p. 51.5°–52.5° C) prepared from palmitic acid of high purity according to the method of Schwenk, E. and Papa, D; J. Am. Chem. Soc., 70 (1948) 3626, was treated with a solution of potassium hydroxide in 95 % methanol in an oil bath at 90° C at which 2-hydroxyhexadecanoic acid (m.p. 86.1°–86.3° C after recrystallization from ethanol and then from dichloromethane) was formed. Methyl 2-methoxyhexadecanoate (m.p. 28.6°–30.6° C) was obtained from 2-hydroxydecanoic acid by esterification and etherification with diazomethane using borone trifluoride as catalyst for the esterification whereafter it was reduced with lithium aluminum hydride to the formation of 2-methoxyhexadecanol-1 (m.p. 34.3°–34.9° C) which was purified by chromatography on silicic acid, 2-methoxyhexadecyl p-toluenesulphonate (m.p. 38°–39° C) was prepared by treating 2-methoxyhexadecanol with p-toluenesulphonylchloride in pyridine.

1,2-Isopropylidene glycerol used as starting material may be prepared according to Renoll M. and Newman, M.S.; Org. Syn. Coll. vol. III (1955) 502.

EXAMPLE 4

Preparation of 1-O-(2-ethoxy-hexadecyl)-glycerol

Ethyl 2-ethoxyhexadecanoate. To a solution of sodium ethoxide in ethanol, prepared from sodium (1.46 g) and ethanol (35 ml) a solution of ethyl 2-bromohexadecanoate (20.3 g) in ethanol (25 ml) was added. After refluxing for 3 h water was added and the product was taken up in ether. After evaporation of the ether and fractionation of the residue there was obtained 10.8 g ethyl 2-ethoxyhexadecanoate b.p. 112°–114° (0.01 mm), $n_D^{23}$ 1.4393.

2-Ethoxyhexadecanol-1 was prepared by reduction of the ethyl ester just described with lithium aluminium hydride. Ethyl 2-ethoxyhexadecanoate (6.56 g) dissolved in dry ether (30 ml) was added drop by drop to a solution of lithium aluminium hydride (1.00 g) in dry ether (50 ml) during continuous stirring. After refluxing for 30 min. and cooling the excess of lithium aluminium hydride was destroyed by adding ethyl acetate and then water. The solution was acidified with diluted sulfuric acid and then extracted with ether. There was obtained 5.67 g of a colourless oil, which after purification by silicic acid chromatography with 1 % ether in light petroleum gave 4.0 g which after solidification had m.p. 35.3°–35.7° c.

2-Ethoxyhexadecyl p-toluenesulfonate was prepared by treating 2-ethoxyhexadecanol (1.72 g) with p-toluenesulfonylchloride (1.5 g) in pyridine (2.3 ml) at room temperature over night. There was obtained 2.47 g of a crude product, which by thin layer chromatography was shown to contain very small amounts of impurities.

2,3-O-Isopropylidene-1-O-(2-ethoxyhexadecyl)-glycerol was prepared by condensing the ethoxyhexadecyl p-toluenesulfonate with 1,2-isopropylidene glycerol. To melted and granulated potassium (0.25 g) in dry refluxing benzene (20 ml) 1.2-isopropylidene glycerol (0.85 g) was added. After all the potassium had reacted a solution of 2-ethoxyhexadecyl p-toluenesulfonate (2.20 g) in dry benzene (10 ml) was added. After refluxing over night and extraction with ether there was obtained 2.31 g of a crude product which after silicic acid chromatography with a few percent ether in light petroleum as eluting solvent gave 0.90 g pure 2.3-O-isopropylidene-1-O(2-ethoxyhexadecyl)-glycerol.

1-O-(2-ethoxyhexadecyl)-glycerol. The isopropylidene compound (0.80 g) was treated with a solution of 4 N HCl (1.3 ml) and ethanol (4 ml) at 85° for 2.5 h. The glycerol ether was extracted by ether and purified by silicic acid chromatography. The less polar contaminants were removed by elution with 5% diethyl ether in light petroleum and the free glycerolether was then eluted with ether. 90 % of the crude product consisted of free glycerol ether.

In an analogous manner there was prepared:
1-O-(2-methoxyhexadecyl)-glycerol
1-O-(2-propoxyhexadecyl)-glycerol
1-O-(2-butoxyhexadecyl)-glycerol These compounds have been identified by means of NMR, masspectrometry and infrared spectroscopy.

bicarbonate and 20–40.000 I.U. of penicillin and streptomycin added per 100 ml was used for the cultivation of the He La cells. pH was 7,4 at the beginning of the experiment. The medium was changed 2 times per week. A suspension of He La cells was obtained by treatment with versene. The glycerol ethers were dissolved in the medium in concentrations of 1, 5, 25 and 100 µg/ml. 1,5 ml of cell suspension, containing $10^6$ cells/ml, was added to 18,5 ml medium. The growth was registered by counting the cells in a Burker chamber.

C3H mice or their F1 hybrids were used for the studies of the effect of the glycerol ethers on transplanted mammary carcinoma. These mice were obtained from Jax Mice Lab., USA, in 1962 and developed a spontaneous mammary carcinoma in 1963. Suspensions of tumour cells were prepared by homogenating tumour tissue with a small mesh screen and diluting the homogenate with Hank's solution. About 50.000 cells were injected intramuscularly in one of the hind legs. After about 1 week a tumour of the size of a pea had developed at the site of the injection and the animals were divided in a test group and a control group. Two experi-

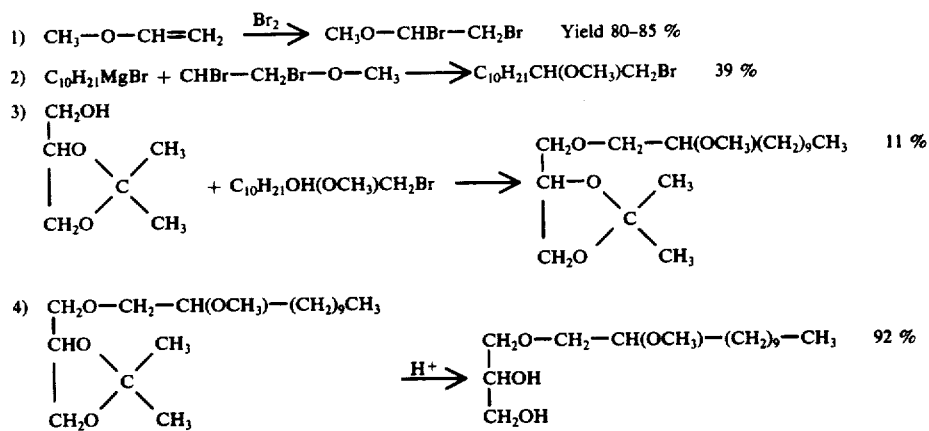

The alkyl group of the glycerol ethers of the present invention are according to one modification built up from smaller groups to the predetermined length prior to the reaction with the glyceryl derivative. This modification is illustrated by the above reaction scheme showing the synthesis of 1-0-(2-methoxydodecyl)-glycerol. This example also gives the yields at the various stages.

Compounds of the present invention have been tested for their antibiotic and cytostatic effects as here described more in detail.

Included in this testing were among others, the following compounds
1-0-(2-methoxyhexadecyl)-glycerol
1-0-(2-ethoxyhexadecyl)-glycerol
1-0-(2-butoxyhexadecyl)-glycerol
1-0-(2-methoxy-4-hexadecenyl)-glycerol
1-0-(2-methoxy-4-octadecenyl)-glycerol All compounds tested were antibiotically active and had an inhibiting effect on the growth of He La cells.

For testing on antibiotic activity a stock solution of glycerol ethers was prepared by dissolving them in a sorensen's phosphat buffer pH 6,5 containing 10% DMSO (dimethylsulfoxide). The activity was measured as minimum inhibiting concentration in meg/ml.

Hank's solution containing 0,5% hydrolysate of lactalbumin, 7% calf serum and with 7 ml 0,15% sodium ments were performed. In the first one the animals in the experiment group were given a pelleted feed with 1% of glycerol ethers from Greenland shark liver oil. In the second experiment 0.5% methoxy-substituted glycerol ethers were included in the diet.

In the diet of the control group the glycerol ethers were substituted by soya oil. After 12 days in the first experiment and 15 days in the second series the animals were killed and the leg tumours were dissected out and weighed. The number of metastases in the lungs was determined in a dissection microscope.

Male Spraque Davley rates were used for the studies on blood cells. The rats were given a diet of 20% protein as fish protein concentrate, 10% peanut oil with 200.000 IU vitamine A, 18.250 IU vitamin D 2,1 g tocophenol and 1 g tocopherol acetate per kg of oil, 61,5% saccarose, 3% cellulose powder, 4,5% salt mixture and 1% vitamin mixture. The rats were housed in individual cages and fed ad libitum. Their mean weight at the beginning of the experiment was about 50 g. The animals were weighed twice per week. After 4 weeks the red and white blood cells were counted in a blood cell counter.

RESULTS

Methoxy-substituted glycerol ethers showed an antibiotic activity against several types of bacteria, especially *Coryne-bacterium hofmanni, Diplococcus pneumoniae, Staphylococcus Oxford, pyogenes* A and *pyogenes* H, *Streptococcus pyogenes* and *Streptococcus viridans*. This was in marked contrast to the ordinary alkoxy group free glycerol ethers which had no antibiotic activity. The antibiotic effect of the methoxy glycerol ethers was inhibited by addition of serum.

The growth of He La cells was studied for different periods of time with methoxy compounds added to the medium (Tables II-V). In the first experiment methoxy glycerol ethers were added in amounts of 100, 25 and 5 µg/ml medium and the experiment was continued for 6 days. The cell counts showed that in the highest concentration used, 100 µg/ml, all cells were dead after 3 days. In a concentration of 25 µg/ml the number of cells was lowered. In these short time experiments the methoxy compounds in a concentration of 5 µg/ml seemed to stimulate the cell growth somewhat. At a concentration of 25 µg/ml morphological changes were observed. Some cells were giant cells and small, round, degenerated cells were also found. The giant cells are usually cells which have lost their mitose activity. At 5 µg/ml there was a slight tendency to giant cell formation from the third day. About the same results were observed for the compounds isolated from Greenland shark liver oil and the synthetic 2-methoxy hexadecyl glycerol ether.

TABLE II.

The effect of methoxy glycerol ethers in concentrations of 100, 25 and 5 µg/ml medium on growth of He La cells. Incubation for 6 days.

| Group | Cell counts | | |
|---|---|---|---|
| | 1 day | 3 days | 6 days |
| Controls | 54 | 122 | 186 |
| *AI a | 65 | All cells dead | All cells dead |
| AI b | 172 | 115 | 168 |
| AI c | 175 | 89 | 212 |
| **AII a | 157 | All cells dead | All cells dead |
| AII b | 206 | 91 | 148 |
| AII c | 201 | 137 | 225 |

AI = Methoxy glycerol ethers isolated from Greenland shark liver oil.
AII = Synthetic 2-methoxy hexadecyl glycerol ether
a = 100 µg/ml
b = 25 µg/ml
c = 5 µg/ml
d = 1 µg/ml

TABLE III.

The effect of methoxy glycerol ethers in concentrations of 25 and 5 µg/ml medium on growth of He La cells. Incubation for 10 days.

| Group | Cell counts | | | |
|---|---|---|---|---|
| | 1 day | 2 days | 6 days | 10 days |
| Controls | 78 | 98 | 228 | 359 |
| AI b | 75 | 97 | 240 | 32 |
| AI c | 67 | 138 | 231 | 279 |
| AII b | 64 | 154 | 160 | 272 |
| AII c | 63 | 113 | 205 | 407 |

TABLE IV.

The effect of methoxy glycerol ethers in concentrations of 25, 5 and 1 µg/ml medium on growth of He La cells. Incubation for 14 days.

| Group | 2 days | 5 days | 8 days | 11 days | 14 days |
|---|---|---|---|---|---|
| Controls | 138 | 172 | 520 | 757 | 649 |
| AI b | 81 | 70 | 0 | 0 | 0 |
| AI c | 118 | 195 | 533 | 502 | 791 |
| AI d | 130 | 199 | 517 | 460 | 651 |
| AII b | 107 | 107 | 241 | 112 | 0 |
| AII c | 113 | 200 | 488 | 546 | 637 |
| AII d | 121 | 271 | 598 | 546 | 557 |

TABLE V.

The effect of methoxy glycerol ethers in concentrations of 5 and 1 µg/ml and of ordinary glycerol ethers in a concentration of 100 µg/ml on growth of the He La cell.

| Group | Cell counts | | | |
|---|---|---|---|---|
| | 0 day | 3 days | 8 days | 6 days after transfer |
| Controls | 139 | 210 | 510 | 176 |
| AI c | | 214 | 490 | 110 |
| AI d | | 269 | 542 | 190 |
| AII c | | 246 | 517 | 136 |
| AII d | | 293 | 498 | 169 |
| B* | | 220 | 523 | 187 |

B = Ordinary glycerol ethers isolated from Greenland shark liver oil.

When the experiments were repeated with 25 and 5 µg/ml of methoxy glycerol ethers and continued for a longer period, viz. 10 days (Table III), methoxy glycerol ethers in a concentration of 25 µg/ml had a marked depressive effect on the cell growth from the sixth to the tenth day. At a concentration of 5 µg/ml the methoxy glycerol ethers had a slight stimulating effect on the cell growth during the first days but inhibited the growth when the incubation was continued. The synthetic product had a similar effect but to a less degree.

In the next experiment the methoxy compounds were used in concentrations of 25, 5 and 1 µg/ml and the incubation was continued for 14 days at 37° C. in a concentration of 25 µg/ml both the methoxy glycerol ethers isolated from Greenland shark liver oil and the synthetic 2 methoxy hexadecyl glycerol ether had a growth inhibiting and later on a cell killing effect (Table IV). At the lower concentrations a slight growth stimulating effect was observed in the beginning of the experiment but after several days' incubation the effect is uncertain due to spontaneous degeneration of the cells. To be able to settle the effect of the low concentrations after a long incubation the effect on the cells after transferring to new culture tubes were studied. After 8 days new cultures were prepared from each group and the cells were counted 6 days after the transfer. A slight tendency to growth stimulation was observed but this was not persistent after the transfer. Six days after the transfer the methoxy glycerol ethers in a concentration of 5 µg/ml had a growth depressant effect but no effect was observed in the lowest concentration of 1 µg/ml (Table V). In this experiment ordinary glycerol ethers from Greenland shark liver oil in a concentration of 100 µg/ml were included but they had no effect on the cell growth.

The whole mixture of glycerol ethers from Greenland shark stimulated the growth of transplanted mammary carcinoma in C3H mice when included to 1% of the diet. On the other hand, the methoxy-substituted glycerol ethers added to the diet in a percentage of 0.5 per cent had an inhibiting effect on the growth of the tumours during a 15 day period (Table VI). There was no difference in body weight between the experimental groups and the controls. The feed consumption was higher in the group given the whole mixture of glycerol ethers than in the controls but in the second experiment with methoxy-substituted glycerol ethers the consumption of feed was the same in the test group and in the controls. Animals with only few metastases in the lungs were more numerous in the group given methoxy-substituted glycerol ethers than in the controls.

TABLE VI.

The effect of glycerol ethers on the growth of transplanted mammary carcinoma in C3H mice.

Experiment I.
Ordinary glycerol ethers. Period: 12 days.

|  | Experimental group | Controls | p |
|---|---|---|---|
| Number of animals | 40 | 40 | |
| Weight of tumour, g (mean ± standard error) | 5.63 ± 0.11 | 4.76 ± 0.24 | <0.01 |
| Food consumption (g/animal/day) | 3.85 | 3.12 | |

Experiment II.
Methoxy-substituted glycerol ethers. Period: 15 days.

|  | Experimental group | Controls | p |
|---|---|---|---|
| Number of animals | 24 | 25 | |
| Weight of tumour, g (mean ± standard error) | 3.4 ± 0.11 | 4.2 ± 0.16 | <0.001 |
| Food consumption (g/animal/day) | 3.41 | 3.57 | |

Ordinary glycerol ethers and methoxy-substituted glycerol ethers each in a concentration of 0.25% of the diet had no effect on the growth of normal rats. The consumption of food was also the same in these groups and in the controls (Table VII). Neither were any statistical differences in red cell counts observed between the test groups and the controls. There was a tendency to an increased number of white blood cells in the groups supplied with ordinary glycerol ethers but no statistical differences could be established between any test group and the controls.

TABLE VII.

The effects of ordinary glycerol ethers and of methoxy-substituted glycerol ethers on weight gain, food consumption, red and white blood cells in growing rats. The compounds were given in the diet in a concentration of 0,25 % for 4 weeks.

|  | Weight gain g | Food consumed g | Red blood cells millions/mm$^3$ M ± SE | White blood cells number/mm$^3$ M ± SE |
|---|---|---|---|---|
| 1. Ordinary glycerol ethers | 175 | 363 | 6.36 ± 0.139 | 16898 ± 861 |
| 2. Methoxy-substituted glycerol ethers | 176 | 369 | 6.19 ± 0.153 | 13370 ± 644 |
| 3. Controls | 180 | 360 | 6.04 ± 0.206 | 14739 ± 920 |

The methoxy-substituted glycerol ethers at the high dosage of 0.25% of the diet had no influence on the red or white blood cell counts. This is of special interest because they inhibited the growth of He La cells in vitro and also decreased the growth of transplanted mammary carcinoma in mice. Thus the methoxy-substituted glycerol ethers have a cytostatic effect on tumour cells without influencing the normal growth or the formation of red or white blood cells, even when given in such a high dosage was 0.25% of the diet.

From the above experiments the following conclusions can be drawn.

1. The methoxy-substituted glycerol ethers were found to differ from the ordinary glycerol ethers in several biological respects.

2. The methoxy glycerol ethers had an antibiotic effect on several strains of bacteria whereas the ordinary ones were inactive.

3. The methoxy compounds but not the ordinary glycerol ethers had an inhibiting effect on the growth of He La cells in vitro.

4. The methoxy compounds inhibited the growth of transplanted mammary carcinoma in mice. The ordinary glycerol ethers, on the other hand, had a growth stimulating effect.

5. The methoxy compounds differed from other substances with cytostatic effect in that respect, that they had no toxic effects on the normal growth or haematopoesis in rats.

6. The methoxy-substituted glycerol ethers offer a new type or substances which might be used for inhibiting tumour growth in patients, possibly in combination with other treatments.

We claim:

1. A pharmaceutical preparation containing as an active ingredient at least one glycerol ether of the formula

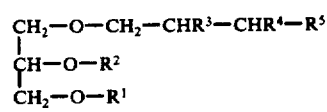

wherein $R^1$ and $R^2$ are the same or different and each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups containing at most 7 carbon atoms, $R^5$ is selected from the group consisting of straight, branched, alkyl and alkenyl groups of 4 to 21 carbon atoms, in association with a pharmaceutically acceptable carrier, said active ingredient being present in an amount of at least 5% by weight, effective to exhibit antibacterial or cytostatic activity.

2. A preparation as claimed in claim 1 wherein $R^1$ and $R^2$ are selected from the group consisting of hydrogen and aliphatic acyl groups of 14 to 18 carbon atoms.

3. A preparation as claimed in claim 1 wherein the active ingredient is present in an amount equal to at least 10% by weight of the preparation.

4. A pharmaceutical preparation as claimed in claim 1 containing as an active ingredient at least 5% by weight of at least one glycerylether of the formula

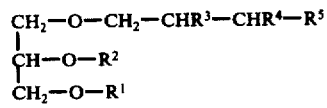

wherein $R^1$ and $R^2$ are both hydrogen, $R^3$ is methoxy, $R^4$ is hydrogen and $R^5$ is selected from the group consisting of straight, branched, saturated and mono- and polyunsaturated alkyl and alkenyl groups of 4 to 21 carbon atoms.

5. A preparation as claimed in claim 1 wherein the active ingredient is 1-0-(2-methoxyhexadecyl)-glycerol.

6. A method for treating infectious bacterial diseases comprising the administration to a host having infectious diseases an effective amount of at least one compound of the formula

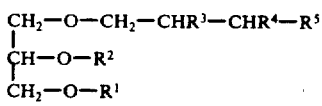

wherein $R^1$ and $R^2$ are the same or different and each is selected from the group consisting of hydrogen and aliphatic acyl groups of at most 24 carbon atoms, one of $R^3$ and $R^4$ is hydrogen and the other is selected from the group consisting of straight, branched, saturated and unsaturated alkoxy groups of at most 7 carbon atoms, and $R^5$ is selected from the group consisting of straight and branched alkyl and alkenyl groups of 4 to 21 carbon atoms.

7. A method as claimed in claim 6 wherein $R^1$ and $R^2$ are the same or different and each is selected from the group consisting of hydrogen and aliphatic acyl groups of 14 to 18 carbon atoms.

8. A method as claimed in claim 6 wherein $R^1$ and $R^2$ in the formula are hydrogen, $R^3$ is methoxy, $R^4$ is hydrogen and $R^5$ is selected from the group consisting of straight, branched, saturated, and mono- and polyunsaturated groups of 4 to 21 carbon atoms.

9. A method as claimed in claim 6 wherein the compound is 1-0-(2-methoxyhexadecyl)-glycerol.

10. A method for inhibiting the growth of tumors comprising administration to a host having tumors of an effective amount of at least one compound of the formula

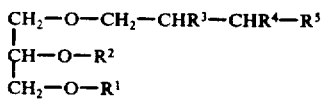

wherein $R^1$ and $R^2$ are the same or different and each is selected from the group consisting of hydrogen and aliphatic acyl groups of at most 24 carbon atoms, one of $R^3$ and $R^4$ is hydrogen and the other is selected from the group consisting of straight, branched, saturated, and unsaturated alkoxy groups of at most 7 carbon atoms and $R^5$ is selected from the group consisting of straight and branched alkyl and alkenyl groups of 4 to 21 carbon atoms.

11. A method as claimed in claim 10 wherein $R^1$ and $R^2$ are the same or different and each is selected from the group consisting of hydrogen and aliphatic acyl groups of 14 to 18 carbon atoms.

12. A method for inhibiting the growth of tumors comprising administration to a host having tumors of a therapeutically effective amount of at least one compound of the formula

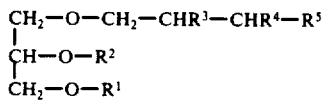

wherein $R^1$ and $R^2$ are hydrogen, $R^3$ is methoxy, $R^4$ is hydrogen and $R^5$ is selected from the group consisting of straight, branched, saturated and mono- and polyunsaturated groups of 4 to 21 carbon atoms.

13. A method as claimed in claim 12 wherein the compound is 1-0-(2-methoxyhexadecyl)-glycerol.

14. A method of antibiotic treatment of bacteria selected from the group consisting of *Corynebacterium hofmannii, Diplococcus pneumoniae, Staphylococcus pyogenes* (A), *Staphylococcus pyogenes* (H Oxford), *Streptococcus pyogenes* and *Streptococcus viridans* comprising administering to a host having said bacteria an effective amount of a compound of the formula

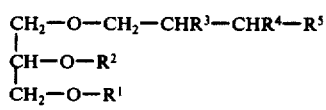

wherein $R^1$ and $R^2$ are the same or different and each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups of at most 7 carbon atoms, and $R^5$ is selected from the group consisting of straight, branched, alkyl and alkenyl groups of 4 to 21 carbon atoms.

15. a method as claimed in claim 14 wherein $R^1$ and $R^2$ are the same or different and each is selected from the group consisting of hydrogen and fatty acid groups of 14 to 18 carbon atoms.

16. A method as claimed in claim 14 wherein $R^1$ and $R^2$ are hydrogen, $R^3$ is methoxy, and $R^4$ is hydrogen.

17. A method as claimed in claim 14 wherein the compound is 1-0-(2-methoxyhexadecyl)-glycerol.

18. A method for inhibiting the growth of carcinoma comprising administering to a host having said carcinoma an effective amount of a compound of the formula

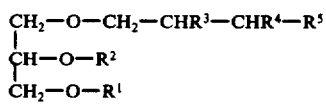

wherein $R^1$ and $R^2$ are the same or different and each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups of at most 7 carbon atoms, and $R^5$ is selected from the group consisting of straight, branched, alkyl and alkenyl groups of 4 to 21 carbon atoms.

19. A method as claimed in claim 18 wherein $R^1$ and $R^2$ are the same or different and each is selected from the group consisting of hydrogen and fatty acid groups of 14 to 18 carbon atoms.

20. A method as claimed in claim 18 wherein $R^1$ and $R^2$ are hydrogen, $R^3$ is methoxy and $R^4$ is hydrogen.

21. A method as claimed in claim 20 wherein the compound is 1-0-(2-methoxyhexadecyl)-glycerol.

22. A method for inhibiting the growth of induced tumors comprising administering to a host having tumors an effective amount of a compound of the formula

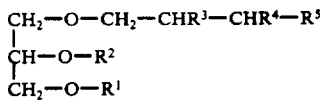

wherein $R^1$ and $R^2$ are the same or different and each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups of at most 7 carbon atoms, and $R^5$ is selected from the group consisting of straight, branched, alkyl and alkenyl groups of 4 to 21 carbon atoms.

23. A method as claimed in claim 22 wherein $R^1$ and $R^2$ are the same or different and each is selected from the group consisting of hydrogen and fatty acid groups of 14 to 18 carbon atoms.

24. A method as claimed in claim 22 wherein $R^1$ and $R^2$ are hydrogen, $R^3$ is methoxy and $R^4$ is hydrogen.

25. A method as claimed in claim 22 wherein the compound is 1-0-(2-methoxyhexadecyl)-glycerol.

26. A method for inhibiting the growth of induced carcinoma comprising administering to a host having said carcinoma an effective amount of a compound of the formula

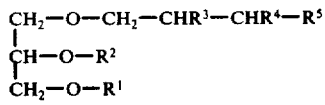

wherein $R^1$ and $R^2$ are the same or different and each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups of at most 7 carbon atoms, and $R^5$ is selected from the group consisting of straight, branched, alkyl and alkenyl groups of 4 to 21 carbon atoms.

27. A method as claimed in claim 26 wherein $R^1$ and $R^2$ are the same or different and each is selected from the group consisting of hydrogen and fatty acid groups of 14 to 18 carbon atoms.

28. A method as claimed in claim 26 wherein $R^1$ and $R^2$ are hydrogen, $R^3$ is methoxy and $R^4$ is hydrogen.

29. A method as claimed in claim 26 wherein the compound is 1-0-(2-methoxyhexadecyl)-glycerol.

30. A method for inhibiting the growth of HeLa cells comprising subjecting said cells to an effective amount of a compound of the formula

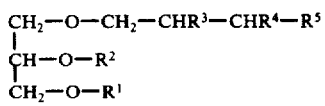

wherein $R^1$ and $R^2$ are the same or different and each is selected from the group consisting of hydrogen and aliphatic acyl groups of at most 24 carbon atoms, one of $R^3$ and $R^4$ being hydrogen and the other being selected from the group consisting of straight, branched, saturated and unsaturated alkoxy groups of at most 7 carbon atoms, and $R^5$ is selected from the group consisting of straight, branched, alkyl and alkenyl groups of 4 to 21 carbon atoms.

* * * * *